United States Patent [19]
Kane et al.

[11] Patent Number: 5,820,767
[45] Date of Patent: Oct. 13, 1998

[54] METHOD FOR QUANTITATION OF MICROORGANISM CONTAMINATION OF LIQUIDS

[75] Inventors: Jeffrey Francis Kane, Trenton; Noel Tod Borton, Chelsea, both of Mich.

[73] Assignee: PALL Corporation, East Hills, N.Y.

[21] Appl. No.: 681,634

[22] Filed: Jul. 29, 1996

[51] Int. Cl.$^6$ ............................. B01D 21/26; C12M 3/00
[52] U.S. Cl. ..................... 210/787; 210/794; 210/435; 210/493.5; 435/4; 435/7.2; 435/30
[58] Field of Search ................. 210/435, 493.1, 210/493.5, 787, 791, 794; 435/4, 7.2, 30

[56] References Cited

U.S. PATENT DOCUMENTS

| | | | |
|---|---|---|---|
| 4,693,985 | 9/1987 | Degen et al. | 210/493.1 |
| 4,895,805 | 1/1990 | Sato et al. | |
| 5,174,896 | 12/1992 | Harms, II | 210/493.5 |
| 5,500,134 | 3/1996 | Chahine | 210/787 |
| 5,527,705 | 6/1996 | Mussi et al. | 435/297.1 |

FOREIGN PATENT DOCUMENTS

| | | |
|---|---|---|
| 0148290 | 7/1985 | European Pat. Off. . |
| 3829028 | 3/1989 | Germany . |
| 5306978 | 11/1993 | Japan . |
| 9428110 | 12/1994 | WIPO . |

OTHER PUBLICATIONS

XP 002051714 Derwent Publication AN 93–409062 (1993).
ASTM Proposal P 229 D–19 "Proposed Test Method for Giardia Cysts and Cryptosporidium Oocysts in Low–Turbidity Water by a Fluorescent Antibody Procedure" 1992 Annual Book of ASTM Standards vol. 11.02, pp. 925–935.
Federal Register vol. 59, No. 28, pp. 6416–6427 (Feb. 10, 1994) U.S. Environmental Protection Agency.
"ELISA Technology", Encyclopedia of Microbiology, vol. 2, pp. 59–62 (1992).
"Polymerase Chain Reaction (PCR)", Douglas H. Jones, Encyclopedia of Microbiology, Ed. S, pp. 443–449, (1991).
"Indirect Fluorescent Antibody Tests and Other Immunomicroscopic Methods", Encyclopedia of Microbiology, vol. 2, pp. 163–164 (1992) J. Lederberg, Ed.
Bailey & Scott's Diagnostic Microbiology, Ellen Jo Baron, et al, pp. 1015–1018 (1994).
"Enzyme Immunoassay", James M. Conroy, et al, Encyclopedia of Microbiology, vol. 3, pp. 87–92 (1992).

Primary Examiner—David A. Reifsnyder
Attorney, Agent, or Firm—Leydig, Voit & Mayer, Ltd.

[57] ABSTRACT

Use of a disposable filtration capsule with a non-occluded membrane filter element in the place of a standard spiral wound cartridge allows for the more rapid and quantitative filtration, recovery, and quantitation of microorganisms in liquid, particularly surface waters, well water, tap water, and the like. The capsule allows a severe reduction in the water sample size tested, substantially minimizes risks of cross-contamination, and provides a leak-proof vessel for shipment. Risk of infection of laboratory personnel and time of analysis are both reduced. Costs of measuring contamination by microorganisms such as Giardia and Cryptosporidium is lowered significantly while increasing the accuracy and dependability of the measurement.

20 Claims, 5 Drawing Sheets

METHOD FOR QUANTITATION OF MICROORGANISM CONTAMINATION OF LIQUIDS

TECHNICAL FIELD

The present invention pertains to a method of capturing, recovering and quantifying microorganism contamination of liquids and apparatus suitable for use therein. More particularly, the present invention pertains to a method of quantifying microorganisms present in water sources through the use of filtration and elution with a unique disposable filtration capsule. The method is particularly applicable to quantitation of Cryptosporidium and Giardia pathogens from lakes, streams, drinking water systems, and the like.

BACKGROUND ART

Protection of the sanitary nature of drinking water is a concern worldwide. While numerous sources of microbial contamination exist, a principle concern is the introduction of pathogenic intestinal protozoa such as Cryptosporidium and Giardia into the water supply. These microorganisms are particularly troublesome, as they are often present in the form of cysts and oocysts. The process of encystment renders the organisms environmentally resistant. Such intestinal pathogens are often introduced into the environment by the direct deposit of human or animal feces (both domestic and feral), or through purposeful or accidental discharge of sewage or wastewater into the lake, stream, or aquifer which supplies raw water to be treated for the purpose of rendering it potable. In addition to testing the drinking water for the presence of microorganisms, tests upstream can often identify the source of contamination. In addition to drinking water tests, tests of water where swimming or bathing is expected is also often necessary to prevent spread of disease, as is illustrated by the closure of much of the Western shore of Michigan's Lake Saint Clair during the summer of 1993 due to fecal contamination from sewage overflow and concurrent weather conditions which maintained rather than ameliorated the contamination in windward areas.

The current proposed test for Cryptosporidium and Giardia is set forth in ASTM D-19 Proposal P229, "Proposed Test Method for Giardia Cysts and Cryptosporidium oocysts in Low-Turbidity Water by a Fluorescent Antibody Procedure." The proposed test method of the Environmental Protection Agency (EPA), United States, was published in 59 FED. REGISTER No. 28, 6416–6427 (Feb. 10, 1994), and is substantially similar to the ASTM P229 method. Both methods are herein incorporated by reference.

In the ASTM P229 method, water to be tested is directed through a cartridge filter containing a spiral wound 25.4 cm (10 inch) long depth filter. The recommended water volume is 380 L (100 gallons), and is directed through the filter cartridge, the nominal 1 $\mu$m spiral wound filter element retaining suspended matter (but see below) and passing the water in which the sediment is suspended. When the necessary quantity of water has traversed the filter, the cartridge is disassembled, and the water present in the cartridge housing and the cartridge itself are transferred to a plastic sample bag, e.g., a Zip-Lock® bag, and preferably double bagged, for transportation to the laboratory.

In the lab, the filter cartridge is cut apart with a knife or scalpel and the yarn wrapping and sediment separated into three portions, an interior, relatively sediment-free portion, an intermediate portion, and an outside, heavily sedimented portion. The yarn in each of these portions is washed successively with the same three 1.0 L volumes of eluting solution, the most interior yarn being washed first. The washing step consists of massaging the yarn in the eluting solutions by hand, or alternatively adding the yarn to a stomaching bag (alternative EPA procedure) and homogenizing in a stomacher followed by hand massaging and homogenizing a second time.

The eluate, containing sediment and any microorganisms trapped by the filter, is centrifuged for 10 minutes at 1050×g in 250 ml centrifuge bottles in a swinging bucket centrifuge, the supernatant discarded to waste and the solids combined, resuspended, and recentrifuged to produce a pellet whose volume is measured, a portion of which is resuspended and tested for the presence of Cryptosporidium and Giardia by standard molecular methods, in this case fluorescent antibody procedures. Additional information relative to these molecular methods as well as other methods which may, in general, be useful is disclosed by Abdallah M. Isa, "Elisa Technology", ENCYCLOPEDIA OF MICROBIOLOGY, Vol. 2, pp. 59–62 (1992); J. Lederberg, Ed., "Indirect Fluorescent Antibody Tests and Other Immunomicroscopic Methods", ENCYCLOPEDIA OF MICROBIOLOGY, Vol. 2, pp. 163–164 (1992); E. Baron, L. Peterson and S. Finegold, DIAGNOSTIC MICROBIOLOGY, Bailey & Scott's; pp.1015–1018; D. Jones, "Polymerase Chain Reaction (PCR)", ENCYCLOPEDIA OF MICROBIOLOGY, Vol. 3, pp. 443–449 (1992); and J. Conroy, R. Stevens and K. Hechemy, "Enzyme Immunoassay", ENCYCLOPEDIA OF MICROBIOLOGY, Vol. 3, pp. 87–92 (1992) which are incorporated by reference.

The prior art methods of testing leave much to be desired. Among the deficiencies are the following:

Filter cartridges and housings from different manufacturers are not fully interchangeable;

Filter cartridges may be installed incorrectly;

Filter housings must be cleaned thoroughly between uses, which is both time-consuming as well as offering the potential for cross-contamination;

Filter "pore size," although nominally 1 $\mu$m, spans a wide range, allowing considerable sediment and microorganisms, if present, to pass through;

Housing water and filter cartridge are stored in plastic bags which are susceptible to leakage through damage or improper closure, presenting both cross-contamination, transportation, and loss of sample risks;

Installation and removal must be performed with protective equipment (latex gloves).

The foregoing deficiencies are associated with the basic nature of the filter cartridge and housing and its use in the field. However, upon arrival at the laboratory, further serious deficiencies arise. For example:

The filter element must be manually cut-apart with a knife or scalpel, which poses a risk of infection to the technician, even when wearing latex gloves;

The washing procedure is laborious and uses a large quantity of eluate;

The washing procedure is inefficient, resulting in relatively low recovery of microorganisms, and in addition is highly variable;

The centrifugation of eluate requires large centrifuge bottles which are preferably discarded after use to avoid cross-contamination; and The combination of centrifuged samples for further concentration runs the risk of sample loss and/or contamination.

The foregoing are but some of the deficiencies associated with the prior art process. As an indication of how much of an impact these deficiencies may have on microorganism quantitation, in a round robin test in which water containing a known quantity of challenge microorganisms was "quantitated" using the proposed ASTM procedure, an average of less than 3% (EPA Contract No. 68-C3-0365, WA No. 2–2, p. 21) of cryptosporidium microorganisms were recovered.

It would be desirable to provide a method of isolation of microorganisms from liquids which minimizes the potential for contamination and cross-contamination; which substantially prevents leakage during shipment; which maximizes sediment and microorganism retention; which is more economical of time and capital; which substantially decreases risk of infection of laboratory personnel; which allows quantitation with smaller sample size; which may provide smaller quantities of eluate with which to work; and which provides the opportunity for greater accuracy and reliability of the quantitation.

SUMMARY OF THE INVENTION

It has now been unexpectedly discovered that the foregoing improvements and others are obtained through the use of a disposable sediment collection filtration capsule having an exposed microporous membrane filter as a sediment retention means, and an internal reservoir for eluate, such that sediment and any microorganisms contained therein may be quantitated without resort to the extensive cartridge-cutting, washing, and large volume centrifugation steps of the prior art.

DESCRIPTION OF THE PREFERRED EMBODIMENTS

The present invention employs a unique disposable filtration capsule to both capture sediment and microorganisms and to provide an eluate containing the same for further testing to quantitate target microorganisms present, if any. The novel aspects of the method of the subject invention thus encompasses the collection through elution and/or centrifugation/concentration steps of a complete quantitation protocol.

The disposable filtration capsule of the present invention employs a surface entrapment filter medium which is fully exposed on the upstream side so as to allow high recovery of microorganisms. By "surface entrapment" is meant that the majority of microorganisms are trapped on or above the surface of the membrane as opposed to penetrating the membrane so as to impede removal. By the term "fully exposed" is meant a membrane which is not covered or occluded by a more porous membrane, prefilter, or the like, which again, would interfere with microorganism removal. A coarse screen, grid, or mesh which provides support or containment for the filter medium but does not substantially impede microorganism recovery is not an occluding cover, and may be a desirable feature of the subject capsules. The membrane may be pleated, planar, or may constitute a hollow fiber bundle or other form of membrane.

The shape and disposition of the filtration membrane may vary, and is critical only insofar as when a pleated membrane, a bundle of hollow fibers or other membrane where upstream membrane surfaces are in close proximity is used, the surfaces must be separated enough to allow high microorganism/particulate recoveries. A tightly pleated filter, for example, with the majority of pleats abutting adjoining pleats is not desirable. A flat, planar membrane, or a flat membrane in a cylindrical configuration are highly suitable, for example, but allow for limited flow rates. Commercially available filters are not suitable, as the pleating is too close, and the filter capsule walls are too close to the filter element to allow the necessary elution volume.

Figure 1:
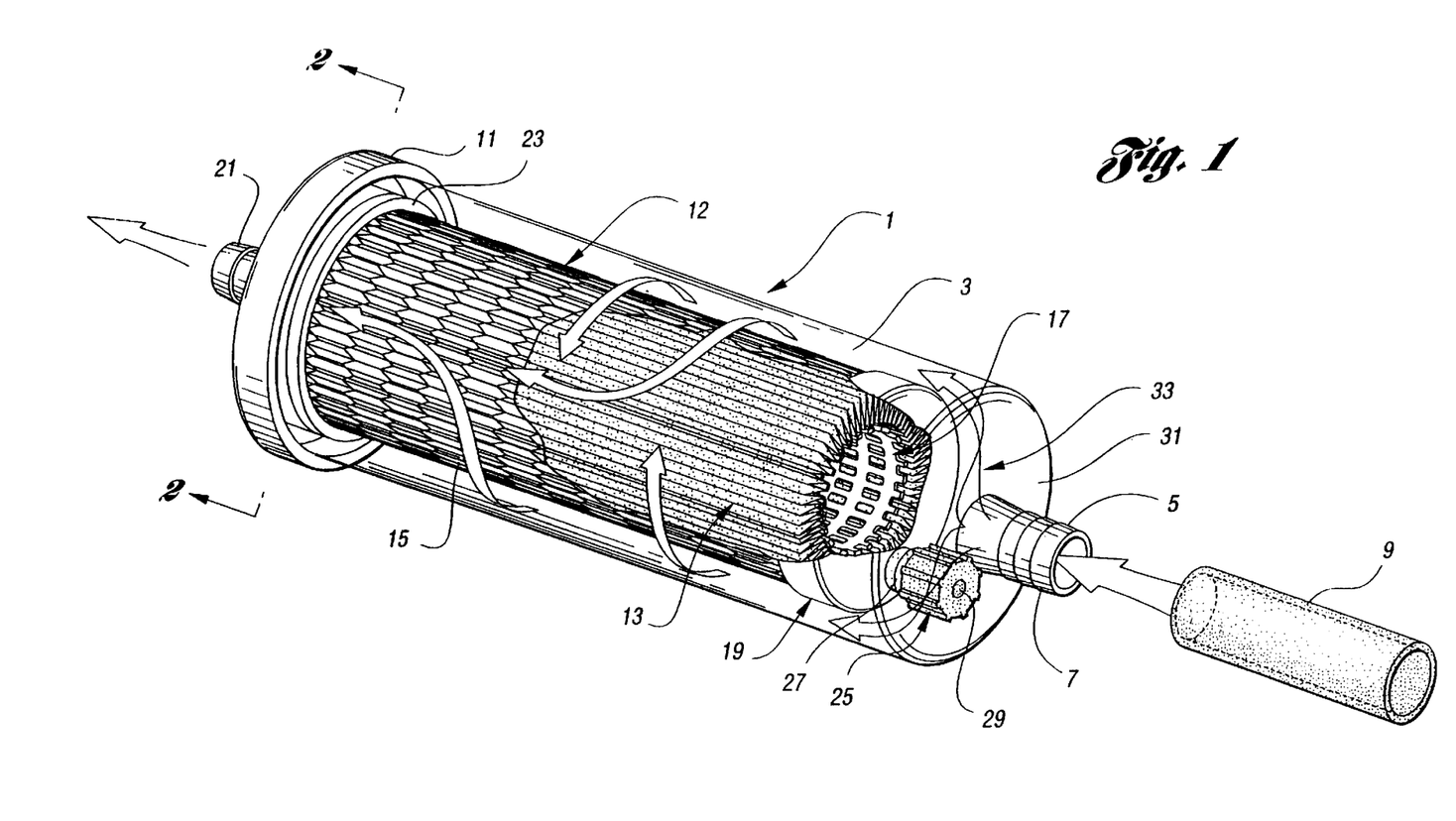
FIG. 1 illustrates one embodiment of a disposable capsule of the present invention as well as fluid flow through the device.

With reference to FIG. 1, one embodiment of a disposable capsule of the present invention is disclosed. In FIG. 1, the capsule 1 is hermetically sealed. The polymer body 3, which is preferably transparent, contains sample (water/sediment) inlet 5 which is molded with ridged tubulatures 7 to assist in sealing to the sample supply hose or tube 9 which may be sealingly connected to the capsule by means of a standard aircraft clamp or equivalent or other sealing arrangement. Alternatively, the sample inlet 5 may be configured as a standard hose fitting, i.e. a male or female screw-type connector.

The capsule housing 3 is hermetically sealed to polymeric end cap 11 by adhesive bonding, solvent bonding, thermal fusion, ultrasonic welding, or other standard bonding/sealing techniques. The integral pleated filtration element 12 comprises loosely pleated microporous membrane 13, which is fully exposed on the upstream side, i.e. is not covered by any occluding prefilter or other occluding surface, to enable sediment trapped on the upstream surface of the filter to be readily eluted, and is contained within optional mesh 15 of plastic or other material. The microporous membrane 13 is supported by rigid support core 17, shown here as a perforated plastic sleeve, and may have a further woven, non-woven, or membrane support located on the downstream side. The upstream, exposed end of integral pleated filtration element 12 is hermetically sealed to end cap 19. Toward the end of the integral pleated filter element which communicates with fluid outlet 21, the element is hermetically sealed to the end cap 11 by being sealed or bonded to the interior surface of radially concentric flange 23. Shown at 25 is an optional air purge vent which is threadedly connected with housing extension 27. The interior of the air purge vent may be filled with elastomeric material to facilitate removal or sampling of contents by means of a syringe through hole 29. Located between the hermetically sealed end cap 19 and the end 31 of the housing 3 is a void volume for containing eluate.

With further reference to FIG. 1, the fluid flow through the capsule of FIG. 1 is shown by broad arrows. Fluid entering the sample inlet 5 flows around and through integral pleated filter element 12 and out outlet 21. Sediment contained in the sample liquid entering the device is trapped between integral pleated filter element 12 and polymeric housing 3, while fluid leaving the device is substantially sediment-free.

Other configurations of the capsule are of course possible. Required are a non-occluded filter element, for example a loosely pleated membrane filter element with no interfering, occluding layer on the upstream side; means for sealing the ends of the element such that fluid flow is totally through the membrane; sample inlet passage communicating with the sample side of the filter element and outlet passage communicating with the filtered side of the filter element; and a void volume of size to contain a sufficient volume of eluate and to allow sufficient agitation to resuspend all or the most substantial portion of the sediment.

Figure 2A:
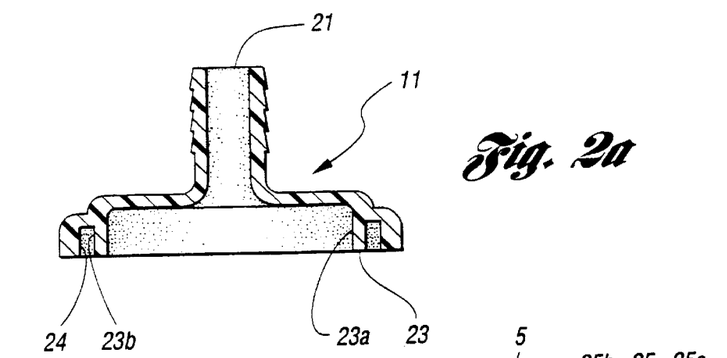
FIG. 2a illustrates a cross-section of an end cap across 2—2 of FIG. 1.

In FIG. 2a is shown a cross-section of an end cap across section 2—2 of FIG. 1. The fluid outlet 21 is within sealing flange 23 to whose inner periphery 23a the filter element is sealed. The housing (3 in FIG. 1) is sealed between surfaces 23b and 24.

Figure 2B:
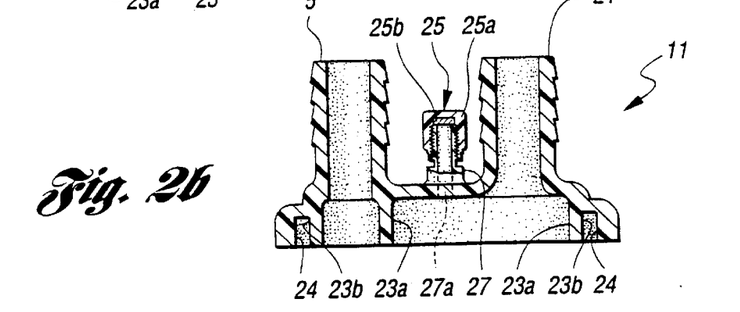
FIG. 2b illustrates a cross-section of an alternative end cap having sample inlets and outlets thereon.

Shown at FIG. 2b is a cross-section of an alternative end cap for use in a polymeric housing as illustrated by 3 in FIG. 1 but which has the sample inlet 5 relocated to the end cap 11. In FIG. 2b, the filter element (12 in FIG. 1) is sealed between sealing surfaces 23a and the polymeric housing (3 in FIG. 1) sealed between sealing surfaces 23b and 24. Located between sealing surfaces 23a and 23b on one portion of the end cap is sample outlet 21. The optional vent may also be relocated to the end cap 11, as shown at 25, with closure 25a containing within it optional elastomeric piercable seal 25b. The closure is threadedly or otherwise sealingly attached to extension 27 which communicates through opening 27a with the upstream side of filter element 12.

Figures 2C, 2D:
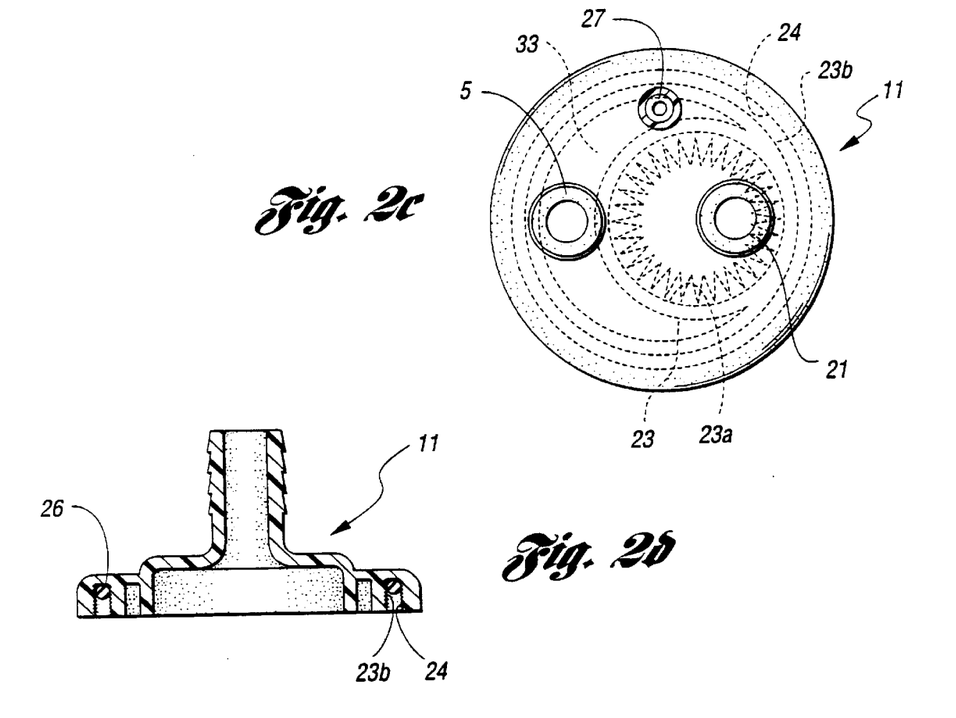
FIG. 2c illustrates the end cap of FIG. 2b in plan viewed from the top (exterior)
FIG. 2d illustrates a removable end cap in cross-section.

FIG. 2c illustrates the end cap of FIG. 2b from the top. The filter element (12 in FIG. 1) is sealed within surface 23a of flange 23. In this case, Flange 23 is not radially symmetric with the outer dimensions of the end cap but is offset so as to provide a longitudinal void volume 33 of crescent-shaped cross-section with which inlet 5 and optional air purge vent extension 27 (shown without closure 25) communicate. The polymeric housing (3 in FIG. 1), now having a closed end where inlet 5 and vent 27 were formerly located, is sealed between sealing surfaces 23b and 24, shown in shadow. Of course, by suitable positioning of the sample inlet 5, outlet 21, and optional vent extension 27, the various sealing flanges may all be made to be radially concentric, and the void volume once again located beyond the hermetically sealed end 19 of the filter element 12.

The cross-section of the filter element may be of any shape consistent with obtaining a good seal with the respective sealing flange on the end cap. Moreover, if the inlet, outlet, and purge vents are all located on the end cap with a longitudinal void volume, then the upstream end of the filter element shown hermetically sealed at 19 in FIG. 1 may be hermetically sealed instead to the end 31 of the polymeric housing 3. It should be emphasized that the void volume performs a dual purpose in not only containing a sufficient amount of elution solution, but also providing enough physical space such that thorough agitation may be implemented. Thus, the term "effective" void volume refers not only to the volume of this void space, but also to the ability to resuspend a significant quantity of sediment, preferably at least 30%, more preferably at least 50%, yet more preferably 70%, and most preferably 90% or more, all without resorting to exceptionally violent agitation or membrane dissection.

Figure 5A:
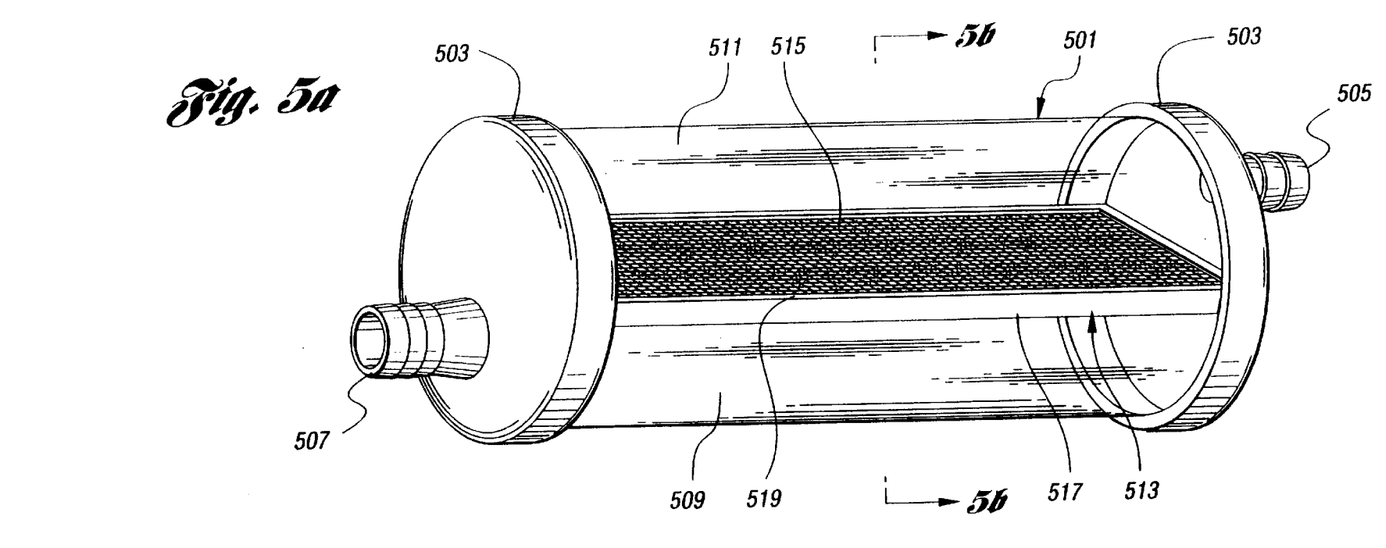
FIGS. 5a and 5b illustrate an alternative embodiment of the subject cartridge.
Figure 5B:
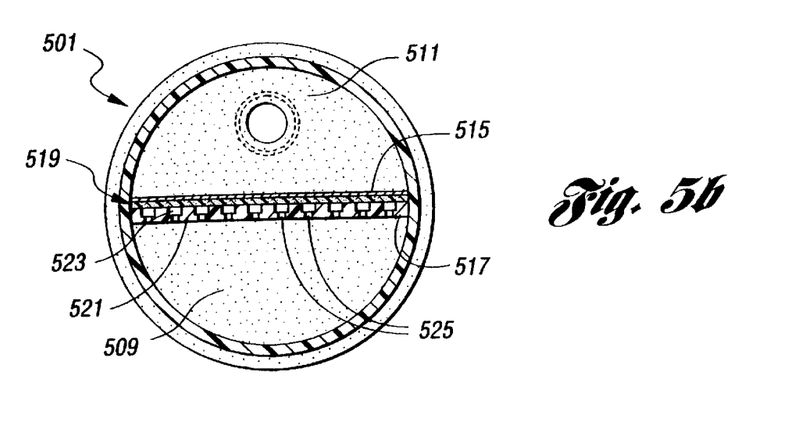

A further embodiment of the subject filter is shown in FIGS. 5a and 5b. In FIG. 5a, a cylindrical capsule consists of cylindrical filter housing 501 and endcaps 503. The endcaps 503 have inlet/outlet tubulatures, the inlet tubulature 505 communicating with inlet/elution reservoir 511, the outlet tubulature 507 communicating with outlet reservoir 509. Filter element 513 comprises a supporting grid 517, a membrane filter 519 and a containment/back flush grid 515. The filter element is shown in cross-section in FIG. 5b.

In FIG. 5b, the filter grid 517 has a plurality of ridges and valleys 521 and 523 to support membrane filter 519. Holes 525 allow filtrate to enter outlet reservoir 509. Atop the membrane 519 on the upstream side is a rigid plastic mesh 515 which allows virtually the entire membrane surface to be unoccluded, yet provides sufficient membrane support to resist temporary back pressure, and particularly to allow back flushing to obtain more complete microorganism recovery. The device shown in FIGS. 5a and 5b need not be cylindrical, but may also be flat or of other shape consistent with ease of manufacture and ability to withstand expected water filtration pressure.

Figures 3A, 3B, 3C, 3D:
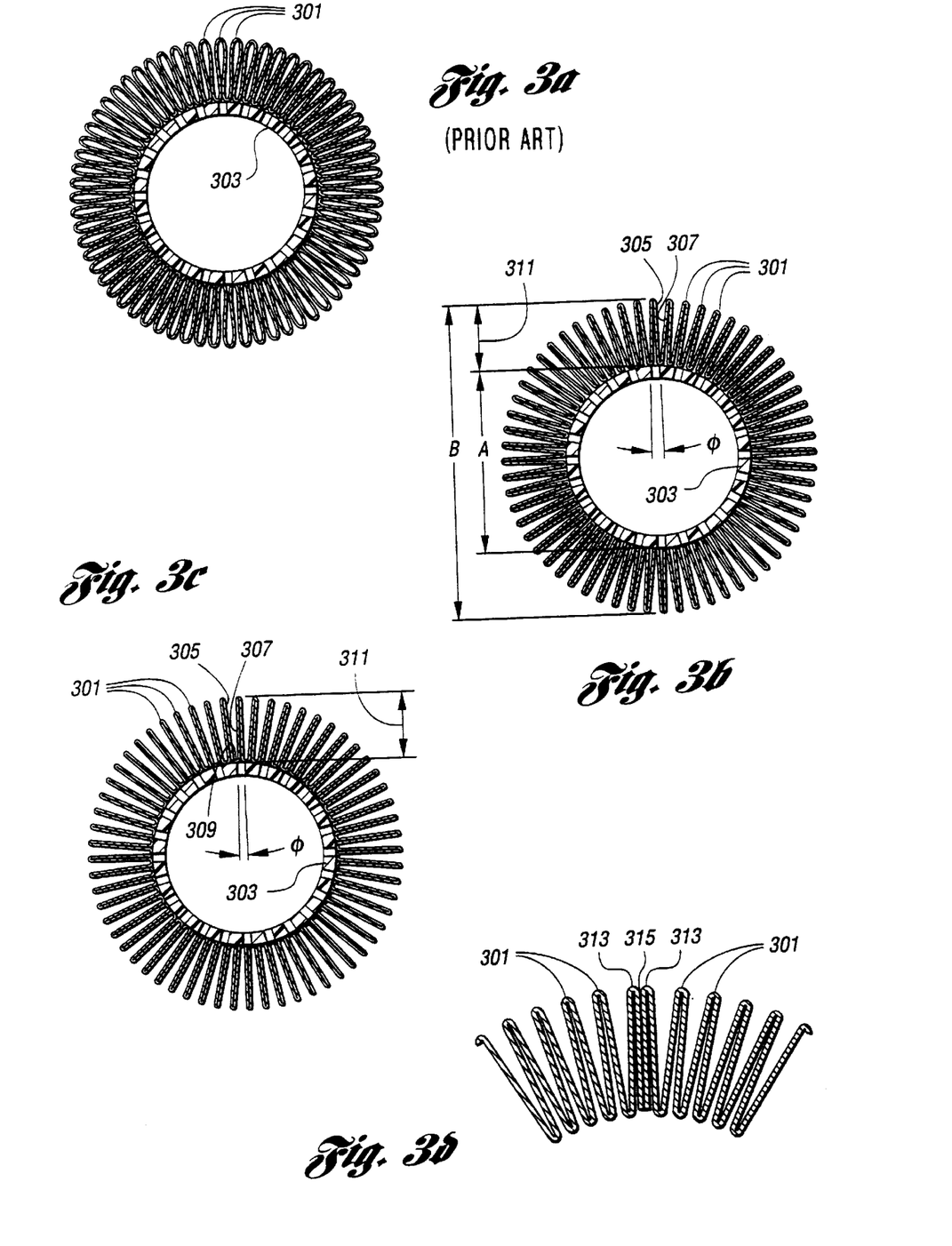
FIG. 3a illustrates the close pleating associated with traditional large volume membrane filters viewed from the end of the membrane filter element.
FIG. 3b illustrates one embodiment of a loosely pleated membrane filter.
FIG. 3c illustrates a further embodiment of a loosely pleated membrane filter.
FIG. 3d illustrates a typical pleat configuration in the vicinity of bonded pleats.

The capsules of the present invention differ notably from other filtration devices. First, the device, in its preferred embodiment, is a hermetically sealed, integral unit. In general, in these types of applications, devices designed for large volume filtration are designed as replaceable filter elements for mounting in a fixed cartridge housing. Second, the pleating of the pleated microporous membrane embodiments is "loose" as hereinafter defined. In conventional filtration elements, the pleats are packed tightly together to maximize filter surface area and thereby increase throughput as well as lengthen time between filter element changes. A conventional configuration is shown at FIG. 3a, where the cross-section of a conventional cylindrical filter element is shown. The filter pleats 301 are arranged radially about macroporous cylindrical support 303, which may be a plastic grid as shown at 17 in FIG. 1a. As can be seen, the pleats substantially abut each other. This abutment is necessary to maximize conventional microporous membrane filter performance. These conventional filters are designed to pass large volumes of liquid while having the smallest size, and therefore the lowest cost, possible. The solids trapped by such filters are to be discarded, and therefore tight packing of the pleats is desirable.

However, in the disposable capsules of the present invention, the flow rate is only important in the sense that slower flow rates will require a longer sediment collection time; the capsule is designed for the purpose of reversibly trapping sediment, not creating high flow for long periods. Most importantly, however, and paramount to the method of quantitating microorganisms defined herein, the sediment and microorganisms must be capable of resuspension and elution from the capsule. In devices such as membrane cartridge filters for water or beverage filtration, the aim is to dispose of the sediment; and whether the sediment is trapped between tight pleats is of absolutely no concern. Here, however, tight pleats would trap sediment and prevent its resuspension and elution. Therefore, it is necessary that when pleats are used, that they be loosely pleated, as shown in FIGS. 3b and 3c.

In FIG. 3b, the pleats 301 are arranged radially around macroporous support 303 as in FIG. 3a, however, the included angle within the pleat (ø) is considerably larger than that shown in FIG. 3a, and thus the walls 305 and 307 of adjacent peaks do not substantially abut each other. The pleat angle is advantageously from 3° to 10°, preferably 4° to 8° and most preferably about 5°–6°. In FIG. 3c, loose pleating is achieved, not by increasing the included angle of the pleat, ø, which remains small, but instead increasing the separation of the pleats by incorporation of a spacing section 309, which may be flat, curved, or of other shape, so long as the bases of the pleat's triangular cross-sections are separated such that again, there is no substantial contact of adjacent pleat walls 305 and 307. The space between adjoining pleats, at the narrowest point, should be of such dimension as to maximize collection of the target microorganism/particulate by preventing the collected "sediment" from wedging between adjoining pleat surfaces precluding recovery.

A loose pleat, in accordance with the above description, may be defined as a series of pleats in which, on the average, contact between the walls of adjacent abutting peaks (e.g. 305 and 307 in FIGS. 3*b*–3*c*) is no more than 25% of the total surface area of the pleat whose height is measured as shown in FIGS. 3*b* and 3*c* as 311. Preferably, the abutting contact is less than 20% of this surface, more preferably less than 10%, and in particular, only incidental contact between adjacent pleats due to irregularities in pleat spacing caused by manufacturing procedures (i.e. essentially no contact). The amount of pleat to pleat contact may be ascertained by visual inspection of the encapsulated end of the cylindrical filter element or by potting the entire element in potting compound, e.g. epoxy, and slicing transverse to filter element length.

The above limitations do not apply to sections of pleating where pleat to pleat contact is necessary for the purpose of bonding the pleated material together at the pleat-parallel seams. This is shown in FIG. 3*d*, where there is substantially no contact between "normal" peaks 301, but there is substantial contact between bonding pleats 313, which are bonded together by adhesive at 315, or by other means, for example by fusion bonding, solvent bonding, etc. The pleat immediately adjacent the bonding pleats may also be distorted, and should be ignored when calculating the degree of pleat to pleat contact. Preferably, with the exception of the bonding pleats and perhaps the next adjacent peaks, one should be able to visually observe the bottom of the valley between adjacent peaks.

An alternative means of defining pleat looseness, or adequate hollow fiber separation, may be based on the recovery of challenge Cryptosporidium and Giardia. To challenge the capsule, from $1\times10^5$ to $5\times10^5$ formalin preserved Giardia and/or $5\times10^4$ to $1\times10^5$ formalin preserved Cryptosporidium are added to 16 L of physiological saline and pumped through or drawn through the capsule at a flow rate between 1000 ml/min and 1500 ml/min, then purged with an additional 2 L of saline solution. The total volume should traverse the capsule in approximately 20 minutes. The capsule is then disconnected, agitated vigorously, i.e. by vortexing, to resuspend sediment (microorganisms) and the liquid emptied into a centrifuge bottle. Two 100 ml elutions are then performed with a 5 minute agitation period for each. The eluates are added to the initial resuspension eluate and a uniform aliquot taken for microorganism quantitation. Alternatively, the combined eluates may be centrifuged to a pellet and the pellet analyzed for microorganisms. If the capsule contains a loosely pleated filter according to the present invention, termed herein "microorganism resuspendable pleating," or by like terms, then the average recovery of Cryptosporidium presented by the challenge should average greater than 9%, preferably greater than 30%, and most preferably above 60%; while the recovery of Giardia should be greater than 9%, preferably greater than 70%, more preferably greater than 85%, and most preferably about 95% or more.

The recovery rates herein are percent recovery of microorganisms in the filtered sample after decanting an initial eluate and two washings with elution solutions and combining the initial eluate and sediment eluates. Measurement is made by counting microorganisms by standard techniques as disclosed in ASTM P229 from uniform portions of centrifuge cake derived from centrifuging the combined eluates as per the ASTM test. A statistically significant number of trials should be used to evaluate the percent recoveries.

The pleating of pleated membranes or the spacing of hollow fiber filters or other filtration devices must be such that substantial recovery of microorganisms and/or particulates may be made when processed as described herein. By the term "effective to allow substantial recovery" as that term applies to microorganisms or particulates, the construction of the filter element should allow minimally about 9% recovery of the target microorganism/particulate, on average. Preferably, recovery should be greater than 30%, and most preferably higher.

The capsule should exhibit an average Giardia recovery rate which is minimally two fold greater than that of a spiral wound filter as specified by ASTM P229, preferably a recovery rate at least 4 times greater, and most preferably, 10 to 40 or more fold greater, the latter values determined at initial flow rates of c.a. 1.25 gal/min for spiral wound filters and c.a. 0.28 gal/min for the capsule, for water having turbidity in NTU between 20 and 70. The sample size in liters for the capsule may be from 5% to 20% of the sample size of the spiral wound filter. Reference may be had for further details to Table 1 herein.

The capsule heretofore described is one which is hermetically sealed and which lends itself to a rapid, economical, and more accurate detection of microorganisms such as Giardia and Cryptosporidium, and which can be used for detection of other microorganisms/particulates as well, provided the membrane pore size is such so as to substantially retain the microorganisms of interest on the upstream surface. The capsule may be used for detection of coliform bacteria, particularly *E. coli*, for example, and for viruses if a charged membrane or other virus retentive membrane is utilized. The integral, hermetically sealed nature of the capsule is a preferred embodiment.

However, the features of the capsule may be substantially maintained while increasing the usefulness and flexibility of the device by including a removable end cap, preferably such that the filter element may be completely exposed. An example of a suitable end cap is shown in cross-section in FIG. 2*d*, which is similar to the end cap shown in FIGS. 1 and 2*a*, except that rather than the polymeric housing 3 being hermetically sealed in the area between end cap surfaces 23*a* and 24, one of the surfaces, in this case surface 24, is threaded to receive a correspondingly threaded end of the polymeric housing 3. At 26 is an elastomeric O-ring seal. Other sealing arrangements are, of course, possible.

The benefit of a removable closure is that access may now be had to the entire membrane. For example, for testing of coliforms, the membrane may be separated, flattened, covered with or contacted with a growth medium and incubated to grow colonies of microorganisms which are too small to observe with traditional fluoroscopic, microscopic, etc., techniques. An example would be coliform bacteria where colony growth in a medium containing suitable chromogenic substrates and enzyme inducers as disclosed in U.S. Pat. No. 5,510,243 may be used to enumerate both total coliforms and *E. coli*. Other techniques are suitable as well, i.e. amplication and hybridization of nucleic acids by PCR, IFA (Immunofluorescence Assay), and the like.

The porosity of the filtration membrane and its composition may be selected with regard to the particular application. Preferably, the membrane is a spontaneously water-wettable membrane such as a polyethersulfone microporous membrane manufactured as disclosed in U.S. Pat. No. 4,900,449, available from Gelman Sciences, Inc., under the trademark SUPOR® microporous membranes. However, other hydrophilic membranes such as those prepared from nylon, cellulose acetate, etc., may be used, as well as hydrophobic membranes which have been treated to render them wettable. The membrane may be ultraporous or microporous dependent upon the size of the target microorganism/particulate. The pore size should be relatively well controlled such that there are no large pores whose size is far in excess of the average. Most conventional filtration membrane materials meet this criterion.

With respect to the pore size of the membrane, the pore size should be such as to retain a substantial amount of microorganism of target size. This pore size is such that minimally 9% of target microorganisms/particulates are retained, preferably greater than 30%, and most preferably, greater than 90%. The degree of retention, or rejection, by the membrane should preferably be such so as to be statistically reliable for a positive/negative (presence/absence) test for a targeted microorganism.

The filter elements and capsule are manufactured by conventional manufacturing techniques. The cylindrical pleated filter may be sealed along its pleat-parallel seam by any means that will assure a seal without damaging the membrane. Among the methods used, some are fusion bonding, solvent bonding, sonic welding, or suitable adhesive, for example an epoxy adhesive. The ends of the cylindrical pleated filter are hermetically sealed, or "potted" again by using the same or similar sealing techniques. Planar membranes may be sealed against a sealing surface by the same techniques, or trapped between knife edge closures, ribbed surfaces, or the like. Hollow fiber membranes may be sealed against a sealing surface using similar techniques.

The capsule, again unlike conventional filters whose housing walls, ends, and end caps, if any, are as physically close to the outer diameter of the pleated membrane as possible in order to reduce manufacturing costs and render the devices as physically small as possible, contains an appreciable void volume, herein termed an "elution-effective void volume."

The elution-effective void volume is a volume which may be minimally 2.2 times the filter volume as defined hereafter, preferably at least 2.5 times the filter volume. Larger void volumes may be used. The filter volume is defined as one-half of the volume occupied by the pleated filter assuming the filter to be in the form of a hollow cylinder having an internal diameter corresponding to the distance between diametrically opposed pleats across a diameter of the macroporous support, and an outside diameter corresponding to the distance between peak ends across an extension of this diameter, e.g. dimensions A (inner diameter) and B (outer diameter) of FIG. 3*b*, and a length defined by the effective length between the seal at the hermetically sealed ends. Thus, for a capsule having a filter element of 2.54 cm inside diameter, 4.45 cm outside diameter, and 12.2 cm length, the filter volume will be approximately 66 cm$^3$, and thus the additional, housing enclosed void volume may range from about 100 ml to about 600 ml, with void volumes in the range of 200 to 300 ml preferred for this size filter. For a flat, planar membrane, the void volume in cm$^3$ should be minimally about 0.5 times the surface area expressed in cm$^2$, and preferably 0.8 to 3 times this surface area.

The void volume may take a variety of shapes. For example, advantageously, a substantial portion of this volume, i.e. 30%, preferably about 50% or more, may be located in a defined space other than merely concentric with the filter element. In other words, the filter element may be substantially offset in the housing as illustrated by the filter element-locating end cap of FIG. 2*c*, providing a volume which is crescent-shaped in cross-section, or may advantageously be located in an extension of the polymeric housing as shown in FIG. 1*a*, where the housing end 31 does not terminate proximate the filter element end cap 19, but rather is somewhat distant, for example 0.75 to 2 inches, providing, for the size filter previously described, a defined reservoir of 100 ml to 200 ml in size. By the term "defined" with respect to void volume is meant that at least 30% of the void volume and preferably about 50% or more be located in a volume which is not radially concentric with the filter element.

The foregoing has been descriptive of the capsule which is preferred for use in the method of the invention. The inventive method pertains to a process of quantitation of fluid-borne microorganisms by flowing a stream of a known ascertainable volume of fluid to be tested into the sample inlet of a disposable microporous membrane filter capsule having a suitable flow rate, for example, but not limited to 0.1 L/min or more at suitable pressure, e.g. 1 bar, wherein the upstream microporous membrane is a loosely pleated membrane not occluded by any further surface which would hamper elution of microorganisms therefrom, the capsule having an elution-effective void volume; removing the disposable capsule from the fluid stream connected to the sample inlet; agitating to resuspend any sediment and/or microorganisms trapped on the upstream side of the filter; decanting an initial eluate of fluid and sediment (unless otherwise specified hereafter, "sediment" includes "microorganisms") from the elution-effective void volume and other upstream internal space; adding to the capsule an elution solution in an amount less than the total upstream internal volume; vigorously agitating the capsule to loosen membrane bound sediment; decanting the elution solution as a sediment eluate; repeating elution solution addition, agitation, and decanting, if necessary, to obtain substantially complete removal of sediment; and preferably combining the initial eluate and the sediment eluate(s) to form a combined eluate; optionally concentrating the sediment eluate and/or initial or combined eluate(s) to recover a concentrated sediment eluate; and optionally, quantifying at least one microorganism present in the sediment eluate or concentrated sediment eluate.

A suitable capsule which may be used in the above method has a filter volume as previously defined, of about 66 ml and a void volume of about 130–150 ml. Both larger and smaller devices may be used as well. One embodiment, suitable for the quantitation of Giardia and/or Cryptosporidium, may be described with reference to a filter capsule as illustrated in FIG. 1, having a filter element containing a loosely pleated microporous membrane filter element having an inside diameter of about 2.2 cm, an outside diameter of about 4.45 cm, and a length of 12.2 cm, a surface area of c.a. 1400 cm$^2$, and a defined void volume of about 140 ml, total upstream volume of c.a. 264 ml (including volume occupied by fluid between pleats on the upstream side). The membrane is a polyethersulfone, inherently wettable membrane having a pore size of 1.0 $\mu$m and available from Gelman Sciences as SUPORO®1200 microporous membrane. The membrane should reject a substantial portion of the sediment.

Having generally described this invention, a further understanding can be obtained by reference to certain specific examples which are provided herein for purposes of illustration only and are not intended to be limiting unless otherwise specified.

Figure 4:
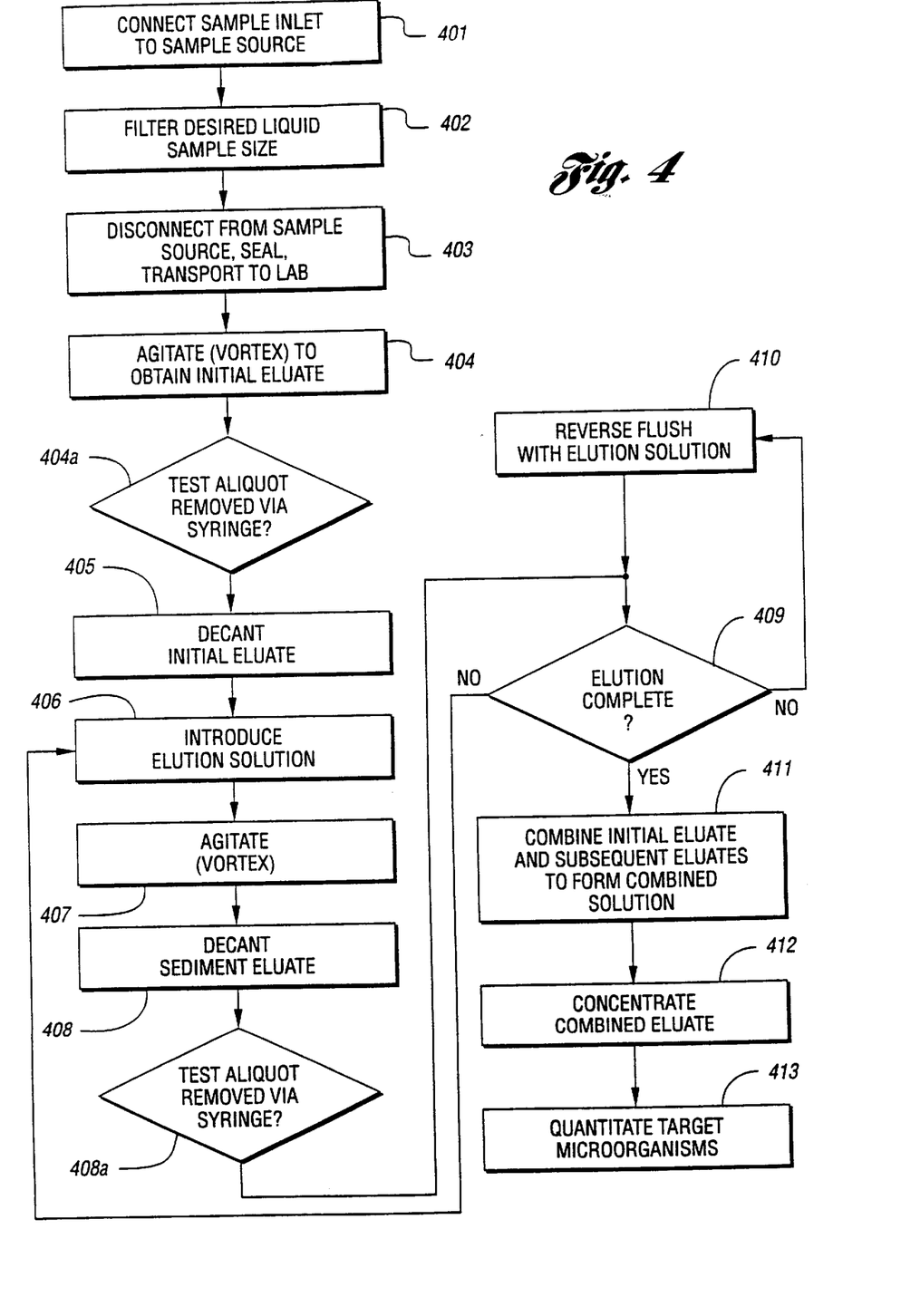
FIG. 4 is a schematic of one embodiment of the method of quantitation of the present invention.

The method may be illustrated by the numbered steps in FIG. 4, which is for purposes of understanding the method generally. Some of the steps, as indicated herein, are optional, and additional steps may be added where necessary. The use of the disposable filtration capsule makes the process more flexible than the use of cartridge filters. For example, an aliquot may be removed from the eluate reservoir at any time; for example, following initial agitation of retained sediment or after one or more additional sediment elutions. The wound filter cartridge method does not offer this advantage.

In FIG. 4, at 401, the sample inlet of the disposable filtration capsule is connected to the sample source. Next, at 402, the desired liquid sample size is filtered through the capsule. At 403, the capsule is disconnected from the sample source, generally sealed, and transported to the lab, which is usually distant from the sample source. Following arrival at the lab, the capsule is agitated 404 to resuspend the sediment collected during the sampling and to obtain therefrom an initial eluate which contains the bulk of the sediment retained. This initial eluate is then decanted at 405 into a suitable vessel, for example a centrifuge bottle. In some cases, decantation of the initial eluate may be sufficient to make a test for the microorganisms desired. However, usually it is necessary to further eluate the capsule with elution solution. In step 406, elution solution is introduced into the capsule, the amount generally less than the total internal volume such that turbulence can be created during agitation. At 407, the capsule is agitated and at 408, a sediment eluate, generally containing a relatively minor amount of sediment, including any sediment contained therein which had been strongly adhered to the filter membrane surface, is decanted. At this point, again, the particular test protocol may indicate that elution is sufficient for analytical purposes and quantitation may take place. However, in general, a further elution with one or more elution solutions or optionally, as shown by decision block 409, a reverse flush with elution solution at 410 may be used to more fully remove any particulate matter and/or microorganisms which may have either strongly adhered to the filter membrane surface, or have been trapped in its pores.

If the elution of sediment is considered complete, then quantitation may be made of any of the eluates collected. However, in general, the initial eluate and subsequent eluates are combined to form one combined eluate at 411, following which these eluates may be concentrated at step 412. Concentration may take the form, for example, of centrifuging one or more eluates followed by resuspending the pellets derived from the centrifuging in a smaller volume of solution and recentrifuging. This method is utilized in the ASTM P229 test for example.

Finally, quantitation of target microorganisms is performed. Although the quantitation step 413 is a part of the method of the subject invention, the details are not critical and may be selected with regard to the particular test envisioned by the protocol. At 404a and 408a are shown optional steps of testing aliquots derived from the elution chamber void volume by removing an aliquot using a hypodermic syringe. In 408a, for example, an aliquot may be used to determine qualitatively whether the preceding elution after agitation was sufficient to substantially remove all sediment. The subject method may also be employed to quantitate sediment, for example by gross weight or other methods.

Examples 1 and 2 and Comparative Examples C1 and C2

Two series of samplings employing disposable filter capsules of the subject invention were used under high turbidity conditions to quantify Cryptosporidium and Giardia in water samples. The two series differed in that the first series of tests were performed on water having a turbidity of 22 ntu, while in the tests of the second series, the turbidity was higher, at 62.6 ntu. The filters were tested against a standard spiral wound polypropylene filter (Filterite model U1A1OU) the type of cartridge filter specified by ASTM P229. The water samples were obtained from the Chattahoochee River.

The proposed ASTM P229 test procedure was modified as indicated in Table 1 below, and employed a microscope slide smear rather than collection on a cellulose acetate disk filter to enumerate microorganisms. The ASTM P229 Information Collection Rule allows a maximum sediment to be processed over the Percoll/sucrose gradient of 1 ml.

High turbidity water was flowed through the respective filters. The wound polypropylene filters were removed, cut apart, washed and stomached as in the EPA proposed test for Giardia and Cryptosporidium. The capsules of the subject invention were agitated (vortexed) for 5 minutes, the sediment eluted to form an initial eluate, and the upstream portion (sediment side) of the capsule washed twice with 100 ml phosphate buffer elution solutions, each time with 5 minutes agitation, to form two successive eluates. The initial eluate and the subsequent eluates were combined, centrifuged as by the ASTM P229 protocol, the supernatant discarded to waste, and the sediment pellet resuspended and concentrated by a second centrifuging. The sampling parameters and results are presented in Table 1 below.

As can be seen from Table 1, although the disposable capsule filters used in Examples 1 and 2 were only used to collect approximately 20% and 5%, respectively, of the volume collected by the wound filter in parallel comparative tests C1 and C2, the sediment collected per liter was higher by a factor of 1.86 and 1.3 respectively, and the Giardia recovery was 17.6 fold and 5.9 fold higher, respectively. Thus, for the inventive method, the sensitivity for detecting Giardia is unexpectedly increased by a factor of roughly 6 to 18 while the sample volume processed was considerably less; the unconcentrated resuspended sediment (initial eluate, sediment eluate) far less (c.a. 300 ml versus c.a. 3 L); and the percentage of sediment pellet utilized for quantitation greater (which should result in greater reliability). No Cryptosporidium was detected in any of the samples.

Example 7 and Comparative Example C3

A disposable capsule filter of the subject invention and a filter meeting the requirements of ASTM P229 (Filterite, U1A1OU) were used to test for Giardia and Cryptosporidium Oocysts in Lake Champlain water. The results are presented in Table 3 below.

TABLE 1

| | WATER | | | | | SEDIMENT | | | | GIARDIA | | |
|---|---|---|---|---|---|---|---|---|---|---|---|---|
| Example | Total Vol (gal) | Total Vol (L) | Flow Rate (gal/min) | Turbidity | Volume Processed (L) | Sediment Recovered (mL) | Relative Sediment per 100 L | Relative Recovery (PP) | Amount Processed (mL) | Amount Processed (%) | Prdicted Giardia per 100 L | Giardia Relative Recovery |
| C1 | 50.2 | 189.9 | 1.25–1.03 | 22.0 | 189.9 | 2.6 | 1.37 | 1.0 | 1.0 | 38.5 | 14.6 | 1.0 |
| 1 | 11.4 | 43.1 | 1.0–0.18 | 22.0 | 43.1 | 1.1 | 2.55 | 1.86 | 0.6 | 54.1 | 257.3 | 17.6 |
| C2 | 100.0 | 378.7 | 1.25–1.03 | 62.6 | 378.7 | 7.4 | 1.95 | 1.0 | 1.0 | 13.5 | 68.5 | 1.0 |
| 2 | 5.2 | 19.7 | 0.28–0.09 | 62.6 | 19.7 | 0.5 | 2.54 | 1.3 | 0.25 | 50.0 | 405.7 | 5.9 |

Examples 3–6

Four disposable capsule filters of the subject invention were challenged by spikes of Giardia and Cryptosporidium and processed as disclosed previously. Detection limit is 5 organisms; BDL=below detection limit. All values were rounded down for reporting. The results are presented in Table 2 below.

TABLE 2

| | | # of Organisms Injected | | # of Organisms Recovered from Gelman Prototype | | # of Organisms Detected in Effluent | | Percent Recovery | | Average Percent Recovery | |
|---|---|---|---|---|---|---|---|---|---|---|---|
| Example | Water Type | Giardia | Cryptosporidium | Giardia | Cryptosporidium | Giardia | Cryptosporidium | Giardia | Cryptosporidium | Giardia | Cryptosporidium |
| 3 | Buffered Deionized Water | $4.5 \times 10^4$ | $7.0 \times 10^3$ | $3.8 \times 10^4$ | $1.0 \times 10^4$ | BDL | BDL | 84% | 126% | 90% | 95% |
| 4 | Buffered Deionized Water | $4.9 \times 10^4$ | $1.4 \times 10^4$ | $4.7 \times 10^4$ | $9.1 \times 10^3$ | 5 | BDL | 96% | 65% | | |
| 5 | Raw Surface Water | $2.7 \times 10^4$ | $8.7 \times 10^3$ | $1.6 \times 10^4$ | $6.3 \times 10^3$ | 5 | BDL | 59% | 72% | 79% | 65% |
| 6 | Raw Surface Water | $5.4 \times 10^4$ | $1.7 \times 10^4$ | $1.7 \times 10^4$ | $5.6 \times 10^4$ | BDL | BDL | 100% | 59% | | |

As can be seen from Table 2, the recoveries of both Giardia and Cryptosporidium are very high, averaging from 90 to 95% in buffered, deionized water, and 65–79% in raw surface water.

TABLE 3

| Example | Volume Filtered (gallons) | Packed Pellet Volume | Pellet Volume per 100 gallons | Volume Floated | Volume Assayed (sediment equiv.) | Detection Limit per 100 Liters | Results (Expressed per Volume Assayed) | | | |
|---|---|---|---|---|---|---|---|---|---|---|
| | | | | | | | Confirmed | | Unconfirmed | |
| 7 | 74 | 2 mL | 2.7 mL | 1 mL | 1.6 L | 63 | ND | ND | ND | ND |
| C3 | 325 | 3 mL | O.9 mL | 1 mL | 4.4 L | 23 | ND | ND | ND | ND |

ND = not detected
Ex 7 = Capsule of invention, C3 = Filterite
Sample(s) were stained and examined using the protocol of ASTM Method P229. This method employs an immunofluorescent dual monoclonal antibody which is specific for Giardia and Cryptosporidium. Positive controls were stained and examined concurrently.

TABLE 3-continued

| Example | Volume Filtered (gallons) | Packed Pellet Volume | Pellet Volume per 100 gallons | Volume Floated | Volume Assayed (sediment equiv.) | Detection Limit per 100 Liters | Results (Expressed per Volume Assayed) | |
|---|---|---|---|---|---|---|---|---|
| | | | | | | | Confirmed | Unconfirmed |

Notes
Unconfirmed organism: exhibits correct size, shape and fluorescence.
Confirmed Giardia: exhibits all characteristics of unconfirmed organism and exhibits at least two of the following internal structures-axonemes, median bodies, nuclei.
Confirmed Cryptosporidium: exhibits all characteristics of unconfirmed organism and exhibits a minimum of two internal structures known as sporozoites.
Confirmed organisms are not included in the unconfirmed enumeration.
Numbers are reported using significant figures.
Type of Levitant: Percoll Sucrose S.G. of Levitant: 1.10

It is noted that while sampling only 23%, as much water, the inventive method and capsule resulted in 67% of the pellet volume of the standard test. The inventive capsule recovered 2.7 ml sediment/100 gallons as compared to 0.9 ml sediment per 100 gallons for the wound filter.

The filtration parameters of the capsule filter of Example 7 and Comparative Example 3 are given below in Table 4.

TABLE 4

| | Filter Type | |
|---|---|---|
| Parameters | Gelman Prototype (Version 4) | Yarn-wound (ASTM type) Commercial 1 μm |
| Beginning Readings: | | |
| Flow | 2300 mL/min. | 3500 mL/min. |
| Time | 12:10 pm | 12:10 pm |
| Inlet Turbidity | 0.56 NTU | 0.56 NTU |
| Effluent Turbidity | 0.12 NTU | 0.29 NTU |
| End Readings: | | |
| Flow | 150 mL/min | 3500 mL/min. |
| Time | 6:10 pm | 6:10 pm |
| Inlet Turbidity | 0.48 NTU | 0.48 NTU |
| Effluent Turbidity | 0.09 NTU | 0.28 NTU |
| Total Volume Sampled | 74 gallons | 325 gallons |

Examples 8–15

The objective of these experiments was to optimize and automate the extraction of Giardia and Cryptosporidium from the capsule filter. This procedure involved challenging six disposable capsule filters of the subject invention simultaneously with fresh *Giardia lamblia* cysts and *Cryptosporidium parvum* oocysts using a multiport recirculating challenge manifold. The sediment captured by the capsule filters was eluted using two techniques in triplicate using a Lab-Line wrist action shaker. Extracts were centrifuged, stained and microscopically examined using a modified protocol of ASTM P229. Controls were processed concurrently.

Several wrist action shakers were evaluated for their ability to simulate aggressive manual wrist action agitation. A Lab-Line Model 3587-4 was found to be acceptable.

The challenge setup contained a 55 gallon polypropylene reservoir containing the organisms. The organisms were pumped through a digital flow meter, static mixer, multiport manifold and back to the reservoir. The flow rate through the recirculating manifold was kept at a constant 11 gpm. Six capsule filters and two controls were pumped to the multiport manifold and each was equipped with a 1 gpm flow control valve. The effluent of each filter was collected in a 20 liter container.

The 55 gallon reservoir was filled with deionized water and $5 \times 10^6$ of both *Giardia lamblia* cysts and *Cryptosporidium parvum* oocysts. The organisms were obtained as high purity formalin-preserved preparations from Waterborne, Inc. (New Orleans, La.) three days prior to the challenge. The solution of organisms was mixed well followed by recirculating through the static mixer for 15 minutes at 15 gpm.

The multiport manifold was then equipped with six capsule filters and two controls. The controls were 47 mm Teflon in-line filter holders equipped with a 1 μm polycarbonate neutron track etched membrane.

The flow of organisms was initiated through the recirculating system and adjusted to provide an inlet pressure of 36 psi to the filters. After all adjustments had been performed, the valves to each filter were opened and the challenge was started. Each filter was challenged with approximately 20 liters of the mixture. Extract volumes were calculated by weighing the total volume of water collected from the effluent, less the weight of the container itself.

Using a fast recirculating "bleed off" type manifold insured a very homogenous challenge without any bias to flow dynamics, insuring an even challenge to each filter. Two additional controls were collected at the beginning and end of the challenge by bleeding off one liter of challenge solution from the multiport manifold into a 1 liter Teflon container over a 2 minute period.

Each capsule was filled with 120 mL of the following elution buffer:

Single Strength PBS (ASTM P229, PH 7.4)
0.01% Sodium Dodecyl Sulfate (SDS) (w/v)
0.0003% Tween 80 (v/v)
0.015% Antifoam B (v/v)

The concentration of SDS was calculated with consideration to the sodium ions supplied by the PBS and was formulated at 20% of the critical micelle concentration for the denaturation of proteins (Bollag and Edel-stein, PROTEIN METHODS, 1994). Concentrations higher than this may cause undesired protein and/or epitope denaturation and reduce the efficacy of the immunofluorescent antibody staining.

Three of the capsule filters were clamped into the lab line wrist action shaker. The arms of the shaker were adjusted so the filters were in a horizontal position. The shaker was turned on for 5 minutes at 90% the maximum shaking speed. After 5 minutes, the filters were removed from the shaker and the inlet covering was removed. The extract was aseptically poured into a sterile 250 mL conical centrifuge tube.

Again, 120 mL of elution buffer was added to each filter and clamped in the shaker at an orientation of 180 degrees from the previous position. The shaker was again turned on for 5 minutes and the extract transferred to the same 250 mL conical centrifuge bottle.

This process was repeated for the remaining three filters with only one exception (the shaking time was increased to 10 minutes for both agitations).

The 250 mL conical bottles were centrifuged at 1100×g for 20 minutes. All but 40 mL was aspirated to waste. The remaining 40 mL was aseptically transferred to a sterile 50 mL conical centrifuge tube. The 250 mL bottles were rinsed twice with 5 mLs of elution solution and transferred to the corresponding 50 mL tube.

The PCTE membrane filter was aseptically removed from the Teflon filter holder and transferred to 50 mL of elution buffer. The filter was extracted by shaking for 10 minutes, vortexing for 3 minutes with brief sonication in between.

The 1 liter grab samples which were contained in the Teflon bottles did not undergo any processing except buffering with PBS and preserving with 50 mL of 100% formalin.

Quantitative aliquots of all samples were stained in triplicate using the staining procedure of ASTM P229. Organisms were enumerated by complete slide scanning at 300 using fluorescent microscopy.

The following are the results of the Giardia and Cryptosporidium challenge and extraction procedure using shaking times of 5 minutes.

TABLE 6

| Filter # | Organism Types | Challenge Volume | Wrist Action Shaking Time | Average # Recovered (per liter) | Control Average (per liter) | Average % Recovery | Filter Average # Recovery |
|---|---|---|---|---|---|---|---|
| 1 | Giardia lambia | 17.8 L | 5 minutes (×2) | 338 | 489 | 69.1% | 78.8% |
| 9 | Giardia lamblia | 17.4 L | 5 minutes (×2) | 513 | 489 | 105% | |
| 10 | Giardia lamblia | 18.1 L | 5 minutes (×2) | 304 | 489 | 62.2% | |
| 8 | Cryptosporidum parvum | 17.8 L | 5 minutes (×2) | 867 | 2489 | 34.8% | 40.8% |
| 9 | Cryptosporidum parvum | 17.4 L | 5 minutes (×2) | 1482 | 2489 | 59.9% | |
| 10 | Cryptosporidum parvum | 18.1 L | 5 minutes (×2) | 699 | 2489 | 28.1% | |

The control average was determined using grab sample PCTE membrane counts.

The following are the results of the Giardia and Cryptosporidium challenge and extraction procedure using shaking times of 10 minutes.

TABLE 7

| Filter # | Organism Types | Challenge Volume | Wrist Action Shaking Time | Average # Recovered (per liter) | Control Average (per liter) | Average % Recovery | Filter Average # Recovery |
|---|---|---|---|---|---|---|---|
| 11 | Giardia lambia | 19.0 L | 10 minutes (×2) | 405 | 489 | 82.8% | 88.1% |
| 12 | Giardia lamblia | 16.3 L | 10 minutes (×2) | 467 | 489 | 95.5% | |
| 13 | Giardia lamblia | 15.5 L | 10 minutes (×2) | 420 | 489 | 85.9% | |
| 11 | Cryptosporidium parvum | 19.0 L | 10 minutes (×2) | 1426 | 2489 | 57.3% | 51.3% |
| 12 | Cryptosporidum parvum | 16.3 L | 10 minutes (×2) | 1313 | 2489 | 52.8% | |
| 13 | Cryptosporidum parvum | 15.5 L | 10 minutes (×2) | 1087 | 2489 | 43.7% | |

The control average was determined using data from both the grab sample and PCTE membrane sample.

Using the same challenge as previously outlined, the challenge water was inoculated with Hudson River water sediment to a concentration of 1 liter of challenge equaling 40 liters of Hudson River sediment.

The capsule filters were challenged with approximately 18 liters of the challenge mixture and extracted using the Lab Line wrist action shaker model 3587-4 using the 5 minutes procedure for one filter and the 10 minute procedure for the other.

The following are the results of the raw water challenge using the automated extraction procedure.

TABLE 8

| Filter # | Organism Types | Challenge Volume | Wrist Action Shaking Time | Average # Recovered (per liter) | Control Average (per liter) | Average % Recovery |
|---|---|---|---|---|---|---|
| 14 | Giardia lambia | 18.2 L | 5 minutes (×2) | 339 | 489 | 69.3% |
| 15 | Giardia lamblia | 17.3 L | 10 minutes (×2) | 505 | 489 | 103% |
| 14 | Cryptosporidium parvum | 18.2 L | 5 minutes (×2) | 755 | 2489 | 30.3% |
| 15 | Cryptosporidum parvum | 79.3 L | 10 minutes (×2) | 1853 | 2489 | 74.4% |

As can be seen from the Examples and Tables, the use of the disposable filtration capsules in the place of a wound filter provides an exceptionally and unexpectedly high increase in the accuracy of microorganism tests, while providing the advantages of smaller raw sample size, smaller wash (elution) volume, and higher proportion of pellet actually used for testing. In addition, the turbidity of fluid exiting the capsule is low, indicating that a significant amount of sediment is collected, as opposed to the cartridge filter where the effluent remains quite turbid. The ability to collect the sample in a small container readily sealable and not easily subject to transportation damage renders field use far more convenient and reliable. Testing the subject invention capsules with challenge microorganisms of known concentration resulted in consistent recoveries of no less than 28% and, on average, no less than 40% while the proposed ASTM method achieved only about 3% recovery.

The laboratory time saved by eliminating cutting, segmenting, washing, agitating, and multiple centrifuging of large volumes (3 L) is also significant, especially when the lesser risk of infection to laboratory personnel and discarding of hazardous waste is considered.

By the term "further concentration" is meant a process whereby the combined washings or eluates are further concentrated. As indicated in the Examples, this further concentration may involve the centrifugation to a sediment pellet, which may optionally be resuspended and recentrifuged in a smaller volume centrifuge tube to more accurately measure sediment pellet volume if this is necessary.

By the term "quantitation" is meant a method of quantifying microorganisms present. For Giardia and Cryptosporidium, the method of ASTM P229 or the published EPA test method may be used. The molecular techniques described in the publications cited heretofore may also be used. The actual method and details of the quantitation are not part of the inventive subject matter herein with the exception of quantitating using a smear of floated sediment. "Floated sediment" refers to the flotation using Percoll/sucrose solution or its equivalent having a desired specific gravity, for Giardia and Cryptosporidium 1.09–1.10, as described in ASTM test method P229. Quantitation as used herein also refers to a presence/absence test which might otherwise be considered as a qualitative test.

Having now fully described the invention, it will be apparent to one of ordinary skill in the art that many changes and modifications can be made thereto without departing from the spirit or scope of the invention as set forth herein.

What is claimed is:

1. A method for the quantitation of microorganisms in a suspected microorganism-containing fluid sample comprising:

a) connecting a suspected microorganism-containing fluid sample source to a sample inlet of a disposable filtration capsule;

b) flowing a known volume of said suspected microorganism-containing fluid sample through said disposable filtration capsule, said disposable filtration capsule comprising a polymeric housing having a sample inlet and an outlet; positioned between said sample inlet and said outlet a non-occluded filter element comprising a membrane such that all fluid flowing from said sample inlet to said outlet must pass through said filter element and wherein microorganism-containing sediment is trapped on an upstream side of said filter element, said disposable filtration capsule having an elution effective void volume;

c) decanting liquid and the sediment from the upstream side of said filter element through said sample inlet of said disposable filtration capsule in the form of an initial eluate;

d) quantitating one or more target microorganisms from said initial eluate.

2. The method of claim 1 wherein said non-occluded filter element comprises a planar microporous membrane, a support grid adjacent to said microporous membrane downstream from said microporous membrane effective to support said microporous membrane against the pressure of the fluid sample.

3. The method of claim 2 further comprising a containment grid adjacent to said microporous membrane upstream from said microporous membrane.

4. The method of claim 3 wherein said containment grid provides support of said membrane to withstand the pressure of back flushing.

5. The method of claim 2 wherein a void volume in cm$^3$ is at least 0.5 of the surface area of said membrane in cm$^2$.

6. The method of claim 1 further comprising back flushing said filter element prior to the quantitating one or more target microorganisms.

7. The method of claim 1 including adding at least one volume of elution solution to the upstream side of the filter element, agitating said disposable filtration capsule to resuspend at least a portion of any remaining sediment, decanting a sediment eluate comprising elution solution and resuspended sediment, and combining the initial eluate and the sediment eluate to form a combined eluate.

8. The method of claim 1 (g) including centrifuging said combined eluate to form one or more pellet(s) of microorganism-containing sediment.

9. The method of claim 8 wherein said pellet or pellets are resuspended in liquid and recentrifuged to form a recentrifuged pellet.

10. The method of claim 9 wherein said microorganisms are selected from the group consisting of Giardia and/or Cryptosporidium.

11. The method of claim 10 wherein at least a portion of said recentrifuged pellet is used to form a floated sediment, said floated sediment quantitated for the Giardia and/or Cryptosporidium by molecular techniques.

12. The method of claim 1 wherein said filter element comprises a pleated filtration membrane wherein the pleats of said membrane are separated by a spacing effective to allow substantial recovery of microorganisms rejected by said membrane.

13. The method of claim 12 wherein substantially none of the surface areas of adjacent pleats are abutting.

14. The method of claim 12 wherein said pleated filtration membrane includes a series of pleats, each pleat comprising walls and a peak, wherein contact between the walls of adjacent abutting peaks averages no more than 25% of the total surface area of the pleat.

15. The method of claim 1 wherein said filter element comprises a pleated microporous filtration membrane wherein on average not more than 25% of the surface area of adjacent pleats are abutting.

16. The method of claim 1 wherein said filter element comprises a planar filter.

17. The method of claim 1 wherein said filter element comprises a bundle of hollow fiber membranes, said membranes separated by a spacing effective to allow substantial recovery of microorganisms rejected by said filter element.

18. The method of claim 1 wherein said disposable filtration capsule further comprises a separable seal such that upon separating said sail, said filtration element is exposed.

19. A method for quantitating microorganisms in a suspected microorganism-containing fluid sample comprising:
 a) passing a known volume of a suspected microorganism-containing fluid sample through a filtration capsule comprising a housing including a non-occluded filter element having an upstream side and a downstream side, the filter element comprising a membrane, said filter element disposed in the filtration capsule such that all fluid flowing through the filtration capsule passes through the filter element and trapping microorganism-containing sediment on the upstream side of said filter element;
 b) passing from the housing an initial eluate comprising liquid and the sediment from the upstream side of the filter element;
 c) adding at least one volume of elution solution to said upstream side of said filter element, agitating said filtration capsule to resuspend at least a portion of any remaining sediment;
 d) passing from the housing at least one sediment eluate comprising the elution solution and the resuspended sediment from the upstream side of the filter element; and
 e) combining the initial eluate, and the at least one sediment elute to form a combined elute; and quantitating one or more target microorganisms from the combined elute.

20. A method for quantitating microorganisms in a suspected microorganism-containing fluid sample comprising:
 a) passing a known volume of a suspected microorganism-containing fluid sample through a filtration capsule comprising a housing including a non-occluded filter element having an upstream side and a downstream side, the filter element comprising a membrane, said filter element disposed in the filtration capsule such that all fluid flowing through the filtration capsule passes through the filter element and trapping microorganism-containing sediment on the upstream side of said filter element;
 b) passing from the housing an initial eluate comprising liquid and the sediment from the upstream side of the filter element;
 c) adding at least one volume of elution solution to said upstream side of said filter element, agitating said filtration capsule to resuspend at least a portion of any remaining sediment;
 d) passing from the housing a first sediment elute comprising the elution solution and the resuspended sediment from the upstream side of the filter element;
 e) adding at least one additional volume of the elution solution to said upstream side of said filtration element, agitating said filtration capsule to resuspend at least a portion of any remaining sediment;
 f) passing from the housing at least one additional sediment elute comprising the elution solution and the resuspended sediment from the upstream side of the filter element;
 g) combining the initial elute, the first sediment elute and the at least one addition elute to form a combined elute; and
 h) quantitating one or more target organisms from the combined elute.

* * * * *

UNITED STATES PATENT AND TRADEMARK OFFICE
CERTIFICATE OF CORRECTION

PATENT NO. : 5,820,767
DATED : October 13, 1998
INVENTOR(S) : KANE et al.

Page 1 of 2

It is certified that error appears in the above-identified patent and that said Letters Patent is hereby corrected as shown below:

```
Column 20, line 48, after "eluate;" insert --and--;
           line 66, delete "the".
Column 21, line 8, change "1(g)" to --7--;
           line 45, change "sail" to --seal--.
Column 22, line 15, change "elute" (both occurrences) to
--eluate--;
           line 17, change "elute" to --eluate--;
           line 38, change "elute" to --eluate--;
           line 46, change "elute" to --eluate--;
           line 49, change "elute" (both occurrences) to
--eluate--;
           line 50, change "elute" (both occurrences) to
--eluate--;
```

UNITED STATES PATENT AND TRADEMARK OFFICE
CERTIFICATE OF CORRECTION

PATENT NO. : 5,820,767
DATED : October 13, 1998
INVENTOR(S) : Kane, et. al.

It is certified that error appears in the above-indentified patent and that said Letters Patent is hereby corrected as shown below:

line 53, change "elute" to --eluate--.

Signed and Sealed this

Nineteenth Day of October, 1999

Attest:

Q. TODD DICKINSON

*Attesting Officer*     *Acting Commissioner of Patents and Trademarks*